United States Patent

Ghetler et al.

(10) Patent No.: US 9,739,661 B2
(45) Date of Patent: Aug. 22, 2017

(54) INFRARED IMAGING SYSTEM WITH AUTOMATIC REFERENCING

(71) Applicant: Agilent Technologies, Inc., Santa Clara, CA (US)

(72) Inventors: Andrew Ghetler, San Jose, CA (US); Adam Kleczewski, San Francisco, CA (US); Richard P. Tella, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 209 days.

(21) Appl. No.: 14/788,561

(22) Filed: Jun. 30, 2015

(65) Prior Publication Data

US 2017/0003166 A1   Jan. 5, 2017

(51) Int. Cl.
| | |
|---|---|
| *G01J 3/02* | (2006.01) |
| *G01J 3/42* | (2006.01) |
| *G01N 21/27* | (2006.01) |
| *G01N 21/3563* | (2014.01) |
| *G01N 21/55* | (2014.01) |
| *G01J 3/10* | (2006.01) |

(Continued)

(52) U.S. Cl.
CPC ............... *G01J 3/0297* (2013.01); *G01J 3/10* (2013.01); *G01J 3/108* (2013.01); *G01J 3/2823* (2013.01);
(Continued)

(58) Field of Classification Search
CPC .. G01J 3/0297; G01J 3/108; G01J 3/10; G01J 3/2823; G01J 3/42; G01N 21/3563; G01N 21/274; G01N 21/55; G01N 2201/1042; G01N 2201/101; G01N 21/276; G01N 21/4785

(Continued)

(56) References Cited

U.S. PATENT DOCUMENTS

| | | | |
|---|---|---|---|
| 5,377,219 | A | 12/1994 | Geiger |
| 5,757,474 | A | 5/1998 | Sopori |

(Continued)

FOREIGN PATENT DOCUMENTS

| | | |
|---|---|---|
| WO | 2011-142295 A1 | 11/2011 |
| WO | 2014/014469 A1 | 1/2014 |

OTHER PUBLICATIONS

Extended European Search Report dated Nov. 7, 2016, Application No. 16176083.0.

*Primary Examiner* — David Porta
*Assistant Examiner* — Gisselle Gutierrez

(57) ABSTRACT

A method and apparatus for obtaining reference samples during the generation of a mid-infrared (MW) image without requiring that the sample being imaged be removed is disclosed. A tunable MIR laser generates a light beam that is focused onto a specimen on a specimen stage that moves the specimen in a first direction. An optical assembly includes a scanning assembly having a focusing lens and a mirror that moves in a second direction, different from the first direction, relative to the stage such that the focusing lens maintains a fixed distance between the focusing lens and the specimen stage. A light detector measures an intensity of light leaving the point on the specimen. A controller forms an image from the measured intensity. A reference stage is positioned such that the mirror moves over the reference stage in response to a command so that the controller can also make a reference measurement.

14 Claims, 2 Drawing Sheets

(51) Int. Cl.
*G01J 3/28* (2006.01)
*G01N 21/47* (2006.01)

(52) U.S. Cl.
CPC .............. *G01J 3/42* (2013.01); *G01N 21/274* (2013.01); *G01N 21/3563* (2013.01); *G01N 21/55* (2013.01); *G01N 21/276* (2013.01); *G01N 21/4785* (2013.01); *G01N 2201/101* (2013.01); *G01N 2201/1042* (2013.01)

(58) Field of Classification Search
USPC .......................................... 250/252.1, 338.1
See application file for complete search history.

(56) References Cited

U.S. PATENT DOCUMENTS

| | | | |
|---|---|---|---|
| 6,043,506 A | 3/2000 | Heffelfinger | |
| 6,181,474 B1 * | 1/2001 | Ouderkirk | G02B 21/0052 250/252.1 |
| 6,814,933 B2 * | 11/2004 | Vuong | B01J 19/0046 422/82.05 |
| 7,361,898 B2 * | 4/2008 | Mizuno | H01L 22/34 250/252.1 |
| 7,420,664 B2 | 9/2008 | Treado | |
| 7,474,685 B2 | 1/2009 | Kalayeh | |
| 7,791,013 B2 * | 9/2010 | Wang | G01N 21/6452 250/222.1 |
| 8,068,521 B2 | 11/2011 | Weida | |
| 9,546,905 B1 * | 1/2017 | Han | G01J 3/42 |
| 2003/0223072 A1 | 12/2003 | Schulz | |
| 2004/0065832 A1 * | 4/2004 | Cluff | G01N 21/3581 250/341.1 |
| 2006/0082777 A1 | 4/2006 | Drennen | |
| 2009/0218513 A1 | 9/2009 | Bec | |
| 2016/0091704 A1 * | 3/2016 | Hoke | G02B 21/002 348/79 |

* cited by examiner

INFRARED IMAGING SYSTEM WITH AUTOMATIC REFERENCING

BACKGROUND

Quantum cascade lasers provide a tunable mid-infrared (MIR) light source that can be used for spectroscopic measurements and images. Many chemical components of interest have molecular vibrations that are excited in the MIR region of the optical spectrum, which spans wavelengths between 5 to 25 microns. Hence, measuring the absorption of MIR light at various locations on a sample can provide useful information about the chemistry of the sample as a function of position on the sample.

SUMMARY

The present invention includes a method and apparatus for obtaining reference samples during the generation of a MIR image without requiring that the sample being imaged be removed. The apparatus includes a tunable MIR laser that generates a light beam that is focused onto a specimen that is carried on a specimen stage adapted to carry the specimen to be scanned. The stage moves the specimen in a first direction. An optical assembly focuses the light beam to a point on the specimen. The optical assembly includes a scanning assembly having a focusing lens that focuses the light beam to a point on the specimen and a mirror that moves in a second direction relative to the stage such that the focusing lens maintains a fixed distance between the focusing lens and the specimen stage. The second direction is different from the first direction. A first light detector measures a first intensity of light leaving the point on the specimen. A controller forms a MIR image from the first intensity. A reference stage is positioned such that the mirror moves over the reference stage in response to a command from the controller, the controller generating a reference sample measurement when the mirror is over a predetermined location on the reference state.

In one aspect of the invention, the first direction is substantially orthogonal to the second direction.

In another aspect of the invention, the reference stage moves in the first direction in response to a command from the controller.

In another aspect of the invention, the reference stage includes a resolution target.

In another aspect of the invention, the reference stage includes a plurality of samples having different known ratios of specular to diffuse reflections.

In another aspect of the invention, the reference stage includes a plurality of samples having different reflectivities.

In another aspect of the invention, the reference stage includes a sample of a compound having a chemical composition that matches a compound in the specimen.

DETAILED DESCRIPTION

Figure 1:
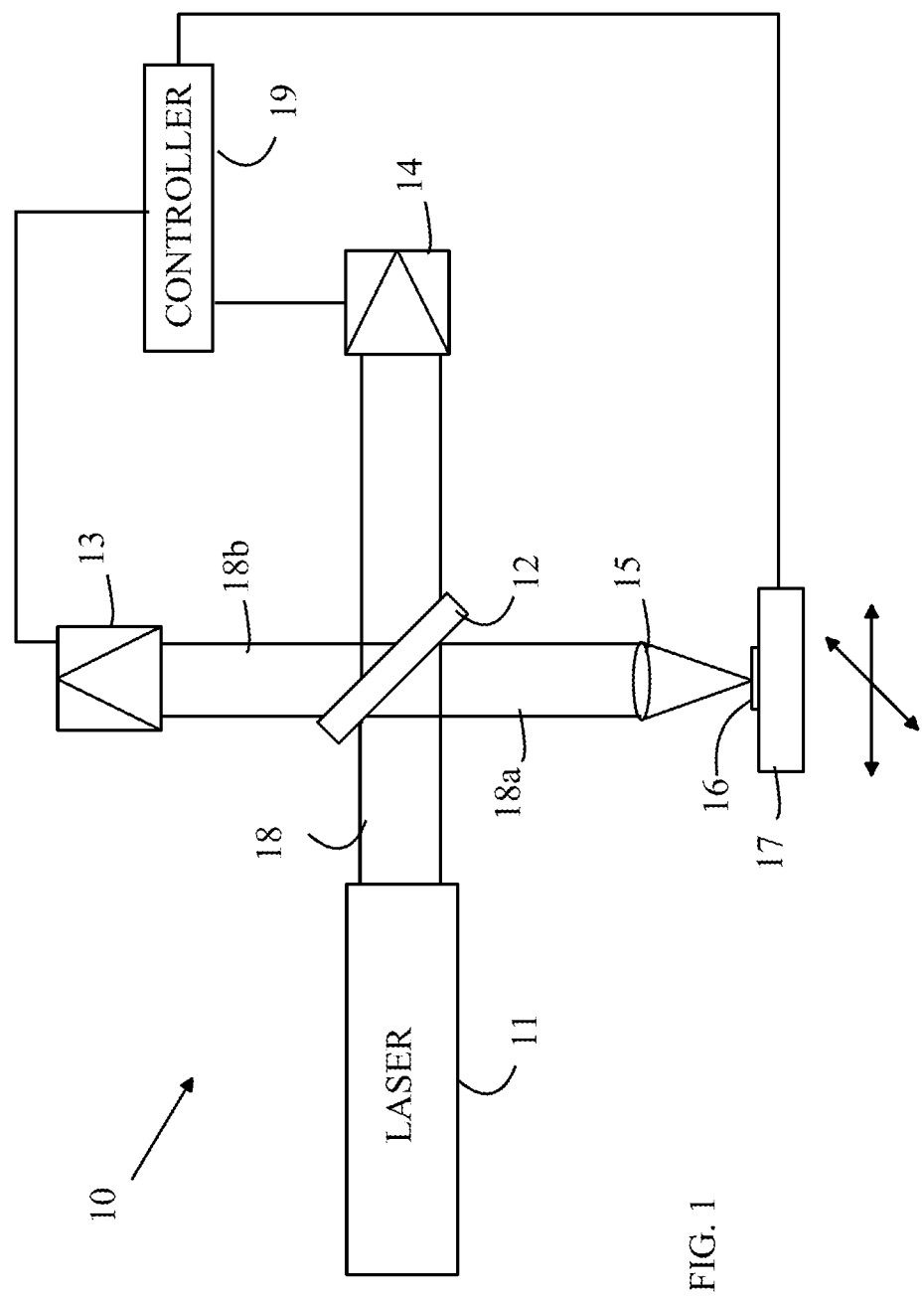
FIG. 1 illustrates one embodiment of a MIR imaging system of the type discussed in this patent application.

Refer now to FIG. 1 which illustrates one embodiment of a MIR imaging system of the type discussed in this patent application. Imaging system 10 includes a quantum cascade laser 11 that generates a collimated light beam 18 having a narrow band of wavelengths in the MIR. In one aspect of the invention, quantum cascade laser 11 is a quantum cascade laser having a tunable wavelength that is under the control of a controller 19. Collimated light beam 18 is split into two beams by a partially reflecting mirror 12. Light beam 18a is directed to a lens 15 that focuses that beam onto a specimen 16 that is mounted on xy-stage 17 that can position specimen 16 relative to the focal point of lens 15. Light that is reflected back from specimen 16 is collimated into a second beam that has a diameter determined by the aperture of lens 15 and returns to partially reflecting mirror 12 along the same path as light beam 18a. While the first and second beams are shown as having the same cross-section in FIG. 1, it is to be understood that the second beam could have a different cross-section than the first beam. A portion of the second beam is transmitted through partially reflecting mirror 12 and impinges on a first light detector 13 as shown at 18b. Light detector 13 generates a signal related to the intensity of light in beam 18b. Controller 19 computes an image as a function of position on specimen 16 by moving specimen 16 relative to the focal point of lens 15 using xy-stage 17.

Controller 19 also monitors the beam intensity of the light in collimated light beam 18 using a second light detector 14 that receives a portion of the light generated by quantum cascade laser 11 through partially reflecting mirror 12. Quantum cascade laser 11 is typically a pulsed source. The intensity of light from pulse to pulse can vary significantly, and hence, the pixels of the image are corrected for the variation in intensity by dividing the intensity measured by light detector 13 by the intensity measured by light detector 14. In addition, since the light intensity from quantum cascade laser 11 is zero between pulses, controller 19 only sums the ratio of intensities from light detectors 13 and 14 during those times at which the output of light detector 14 is greater than some predetermined threshold. This aspect of the present invention improves the signal-to-noise ratio of the resultant image, since measurements between pulses contribute only noise, which is removed by not using measurements between pulses.

This type of imaging system can benefit from measuring the absorption of the incident light as a function of wavelength to create an absorption spectrum at each point in the image. In absorption spectroscopy, the sample is illuminated with light and the amount of light that is reflected from the sample is measured. The process is repeated for a number of wavelengths of the light to generate a spectrum consisting of the intensity of the reflected light as a function of wavelength. The fraction of the incoming light that is reflected from the sample is related to the intensity of the light that was absorbed by the sample. Absorption spectra can be used to identify the chemical compounds in the sample. Hence, an image of a sample in which each pixel of the image includes an absorption or reflection spectrum as a function of wavelength is useful in visualizing the distribution of different chemical compounds in the sample.

The light that is reflected from a specimen depends on the nature of the surface of the specimen. In general, the reflected light is a mixture of specular reflected light from flat surfaces such as the facets of crystals in the sample and diffuse reflected light reflected from rough surfaces or powders. The spectra generated by specularly reflected light differ from those generated by diffusely reflected light. Since many specimens of interest generate a compound spectrum with an unknown ratio of the two types of reflections, interpreting the images in terms of the chemical composition of a sample as a function of position on the sample presents significant challenges. These challenges can be significantly reduced if the contribution of each type of reflection to the measured spectrum at each point in the specimen can be separated.

The specularly reflected light can be separated from the diffusely reflected light by making a number of polarization measurements at each point in the image. Polarized light that is undergoing specular reflection remains polarized. In contrast, diffusely reflected polarized light is depolarized. Hence, the diffusely reflected light can be selectively measured with the aid of a linear polarization filter. If the incident laser light is linearly polarized, the specularly reflected light will be linearly or elliptically polarized. The elliptically polarized light can be characterized by two linear polarizations that are orthogonal to one another as measured on a coordinate system that is fixed relative to the specimen. A linear polarization filter blocks linearly polarized light that has a direction of polarization that is orthogonal to a polarization axis defined on the filter. If a light beam is linearly polarized with a direction that is parallel to that axis, all of the light passes through the filter. If the light beam is linearly polarized along a direction that is orthogonal to that axis, all of the light is blocked. In general, if the light is linearly polarized along an axis that is at an angle of $\theta$ with respect to the polarization axis, the light can be viewed as having a component that is parallel to the polarizer axis and one that is orthogonal to the polarizer axis. The parallel component passes through the filter and the orthogonal component is blocked by the filter. Hence, for an elliptically polarized beam having linearly polarized components $I_s$ and $I_d$ relative to the coordinate system on the sample, part of the light in each component will pass through the filter. The amount of light will depend on the angle between the polarization axis on the filter and the polarization of each linearly polarized component. By making a number of measurements at different relative angles between the polarization axis and the coordinate system on the sample, different combinations of the diffuse and specular light intensity, $I_d$, $I_s$ and $I_p$ can be measured. These measurements can then be combined to obtain the diffuse and specular components.

In general, all forms of MIR spectroscopy require the collection of a reference (background) in order to generate quantitative transmittance, absorbance, or reflectance data. Typically, the background value provides a known response. In the case of transmittance, a sample with a reference sample with a known transmittance is used. Similarly a sample with a known reflectance is used in reflection-based imaging. The measurements are then normalized to the reference samples. The actual substrate used to acquire a reference might vary depending on the type of application. Most changes in acquisition parameters or setup (i.e. objectives, apertures, attenuators) require the acquisition of a new reference. This can be a time consuming process, discouraging users from changing the acquisition parameters. As a result, users often avoid acquiring a new reference which leads to sub-optimum scanning results.

Existing MIR spectrographs require user interaction to initiate and perform the acquisition of the reference. This can lead to a variety of problems as it relies on the user to both perform the reference properly and at regular intervals. This process can be tedious, as it may require removing the sample under analysis, and so users tend to reference less frequently than they should. Other systems demand a user take a reference before every sample and force the user into a predefined procedure to complete the process.

In addition, many infrared spectrometers are purged with dry air or liquid nitrogen. This reduces changes in the environment inside the spectrometer and, hence, reduces the frequency at which a new reference is required. These purge systems, however, can be costly to install and maintain. In addition, changing the reference sample can require that the system be purged repeatedly. Accordingly, it would be advantageous to provide a referencing scheme that did not require the sample to be replaced by a reference sample each time a reference measurement is to be made.

The time needed to complete a scan at one wavelength and polarization can be long if the sample is to be imaged at a high resolution over a considerable region. Accordingly, providing periodic reference scans is advantageous to determine that the system is functioning correctly during the scanning process. The reference samples can include samples having different specular and diffuse reflectivities. The reference samples can also include specific shapes to test the geometric resolution of the scanning system. Finally, the reference samples can include samples with specific chemical compositions to use as background subtraction samples for improving the resolution of the image for some chemical of interest that might be obscured by background chemicals.

A reference system in which the reference samples can be scanned without disturbing the actual sample being imaged is preferred. Repositioning the actual sample without changing its position on the sample stage presents significant challenges. Furthermore, changing the sample can be time consuming, and hence, limits the frequency with which a reference measurement can be made without significantly increasing the total sample scanning time.

Figure 2:
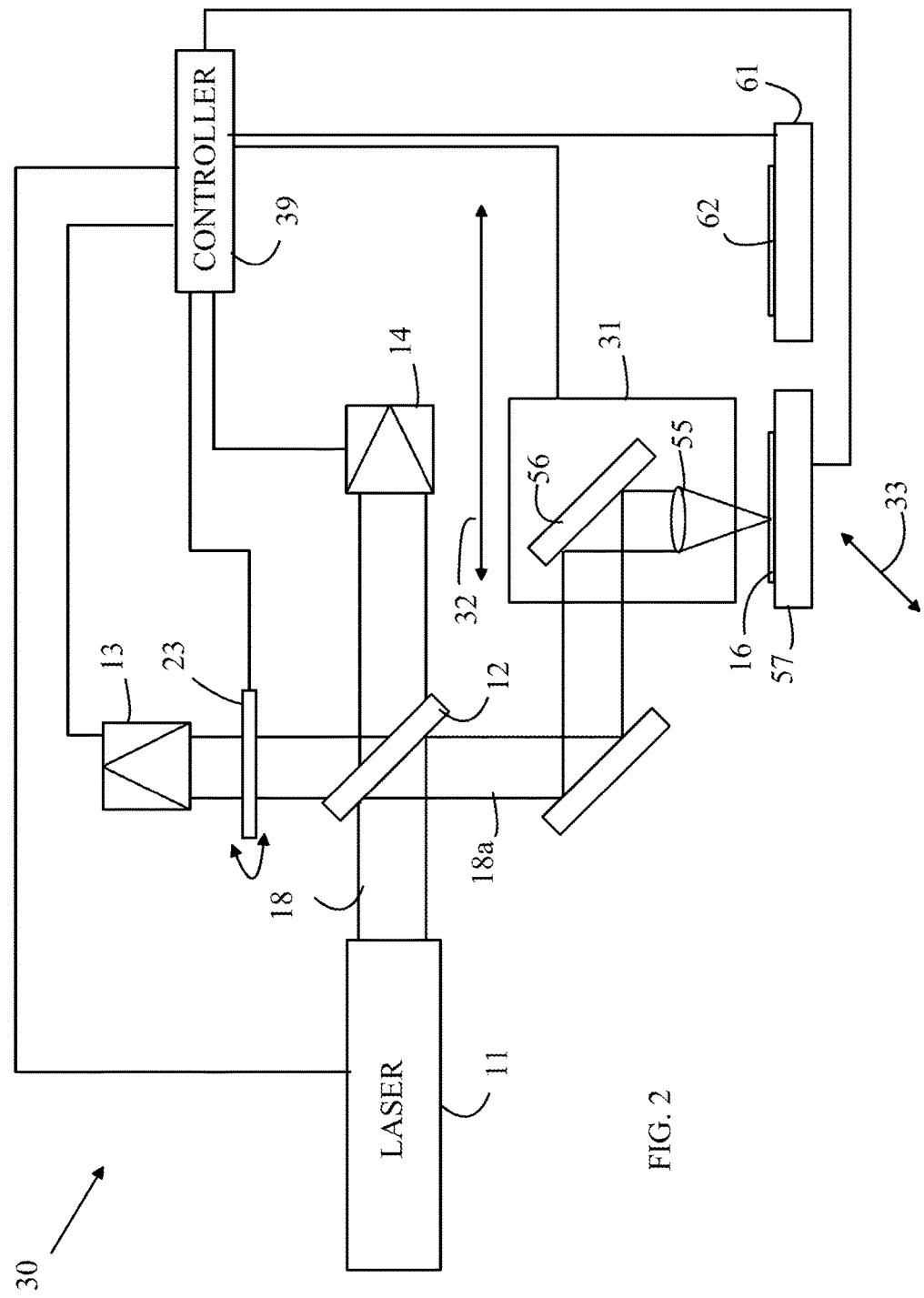
FIG. 2 illustrates another embodiment of an imaging system according to the present invention.

The polarization data must be acquired for each point on the specimen and each wavelength. The order in which the data is taken will depend on a number of factors. If the speed of rotation of the polarization filter is the factor limiting the data acquisition rate, a system in which the polarization is held constant while the stage scans in the x direction has some advantages. In the above described embodiments, the stage moves the sample in two dimensions. However, the stage has a significant mass, and hence, the speed at which the sample is imaged is limited by the motion of the stage. In embodiments in which rapid imaging time is important, embodiments in which the specimen is scanned in one direction by moving lens 15 are preferred. Refer now to FIG. 2, which illustrates another embodiment of an imaging system according to the present invention. In imaging system 30, the stage assembly is divided into two components. Component 31 includes focusing lens 55 and is moveable in a direction shown at 32 such that a single line of the image is generated with each pass of component 31. Since focusing lens 55 and mirror 56 have a mass that is small compared to component 57, component 31 can be moved with much greater speed. In one embodiment, component 31 is mounted on a rail and moved in a manner analogous to a print head on an inkjet printer. The second component of the stage assembly is shown at 57. Component 57 includes the mounting mechanism for the specimen being scanned and moves in a direction 33 that is orthogonal to direction 32. Since component 57 only needs to move once per scan line, the slower speed of motion associated with the more massive component 57 is acceptable. Controller 39 controls the wavelength of quantum cascade laser 11, the axis of linear polarization filter 23, and the position of component 31.

Imaging system 30 includes a reference stage 61 which has a reference target 62 mounted thereon. In one embodiment, reference stage 61 is fixed to the frame of the imaging system and does not move. However, embodiments in which reference stage 61 moves independently in the direction shown at 33 can also be constructed. The direction shown at 33 will be referred to as the "y" direction in the following discussion. The directions shown at 32 will be referred to as the x-direction.

Reference stage 61 is positioned such that component 57 can be positioned over reference target 62 at various locations along the x-direction. Hence, the reference target can be scanned with the actual sample being imaged once per x-scan if desired. Embodiments in which the reference target is scanned less frequently can also be constructed.

As noted above, reference stage 61 can optionally be moved in the y direction in response to commands from controller 39. Such embodiments are useful if "targets" are being scanned in the reference process. The targets can provide information about the spatial resolution of the scanner during the actual scanning process: however, there is a penalty in scanning time, as the x-scan direction is now increased, and hence, the scan requires a longer period of time to be completed. It should be noted that scanning in only the x-direction can also provide information about the resolution of the scanner if it is assumed that the y-direction exhibits a similar resolution.

In addition to providing information about the resolution of the scanner, the targets can include samples of known composition or optical properties to provide a more complex background measurement. For example, a reference could include a series of samples in which the ratio of diffuse to specular reflection changes from sample to sample. Similarly, the reference could include a series of samples in which the reflectivity changes from sample to sample in a known manner. In addition, background samples that include a specific chemical at different concentrations can be used in the target area. The reference image can then be subtracted from the actual sample image to remove background from that chemical to enhance the image so as to detect other features of interest.

A resolution target could also be used on the reference stage. A resolution target includes a series of sharp stripes or squares of known width and different sizes. The rise and fall rates of the signal from the detector while scanning such targets can be used to determine the optical resolution of the system. If it is assumed that the y-resolution is the same as the x-resolution, a series of different widths relative to the scan direction is sufficient, and the reference stage does not need to be moved.

The frequency with which reference samples are scanned depends on the particular application. The frequency of reference scanning depends on commands from the controller 39 shown in FIG. 2. In the extreme case, the reference sample is scanned in each x-direction scan. However, less frequent reference scanning can also be utilized. For example, prior to acquiring infrared data, the optics can be quickly (<1 second) moved over to the reference stage and a reference acquired (<1 second). In this manner, a fresh reference is taken prior to every data acquisition in a matter of a couple seconds.

Each measured reference is validated to ensure it is within the expected range. If any anomalous values are detected, the acquisition is halted and the user informed. A log is automatically kept of the measured reference values to be used for diagnostic purposes at a later time. The system can be predefined to take a reference after a fixed amount of time has elapsed. For example, after 30 seconds a new reference is required, however, any acquisitions within those 30 seconds will share the same reference.

In the above-described embodiments, the sample stage moves in a direction that is substantially orthogonal to the x-direction. However, embodiments in which the x-direction is not orthogonal to the y-direction can be constructed, as long as the controller can determine the coordinate at which the focused beam is applied to the specimen relative to some coordinate system on the sample stage.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An apparatus comprising:
a tunable mid-infrared (MIR) laser that generates a light beam;
a specimen stage adapted to carry a specimen to be scanned, said stage moving said specimen in a first direction;
an optical assembly that focuses said light beam to a point on said specimen, said optical assembly comprises a scanning assembly having a focusing lens that focuses said light beam to a point on said specimen and a mirror that moves in a second direction relative to said stage such that said focusing lens maintains a fixed distance between said focusing lens and said specimen stage, said first direction being different from said second direction;
a first light detector that measures a first intensity of light leaving said point on said specimen;
a controller that forms a MIR image from said first intensity of light; and
a reference stage that is different from said specimen stage positioned such that said mirror moves over said reference stage in response to a command from said controller, wherein
said focusing lens and said mirror move together in said second direction over said specimen stage and said reference stage.

2. The apparatus of claim 1 wherein said first direction is substantially orthogonal to second direction.

3. The apparatus of claim 1 wherein said reference stage moves in said first direction in response to a command from said controller.

4. The apparatus of claim 1 wherein said reference stage comprises a resolution target.

5. The apparatus of claim 1 wherein said reference stage comprises a plurality of samples having different known ratios of specular to diffuse reflections.

6. The apparatus of claim 1 wherein said reference stage comprises a plurality of samples having different reflectivities.

7. The apparatus of claim 1 wherein said reference stage comprises a sample of a compound having a chemical composition that matches a compound in said specimen.

8. A method for obtaining a reference sample during the scanning of a specimen, said method comprising:
providing a tunable mid-infrared (MIR) laser that generates a light beam;
mounting said specimen on a specimen stage adapted to move said specimen in a first direction;

focusing said light beam to a point on said specimen using an optical assembly that comprises a scanning assembly having a focusing lens that focuses said light beam to a point on said specimen and a mirror that moves in a second direction relative to said specimen stage such that said focusing lens maintains a fixed distance between said focusing lens and said specimen stage, said second direction being different from said first direction;

measuring light that leaves said point on said specimen to form a MIR image; and measuring light leaving a reference stage that is positioned such that said mirror moves over said reference stage in response to a command from said controller, said reference stage being different from said specimen stage, wherein said focusing lens and said mirror move together in said second direction over said specimen stage and said reference stage.

9. The method of claim 8 wherein said first direction is substantially orthogonal to second direction.

10. The method of claim 8 wherein said reference stage moves in said first direction in response to a command from said controller.

11. The method of claim 8 wherein said reference stage comprises a resolution target.

12. The method of claim 8 wherein said reference stage comprises a plurality of samples having different known ratios of specular to diffuse reflections.

13. The method of claim 8 wherein said reference stage comprises a plurality of samples having different reflectivities.

14. The method of claim 8 wherein said reference stage comprises a sample of a compound having a chemical composition that matches a compound in said specimen.

* * * * *

UNITED STATES PATENT AND TRADEMARK OFFICE
CERTIFICATE OF CORRECTION

PATENT NO. : 9,739,661 B2  
APPLICATION NO. : 14/788561  
DATED : August 22, 2017  
INVENTOR(S) : Andrew Ghetler et al.

Page 1 of 1

It is certified that error appears in the above-identified patent and that said Letters Patent is hereby corrected as shown below:

On the Title Page

Item (57), in Column 2, in "Abstract", Line 2, delete "(MW)" and insert -- (MIR) --, therefor.

In the Specification

In Column 5, Line 18, delete "process: however." and insert -- process; however, --, therefor.

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*